(12) United States Patent
Nayar (10) Patent No.: US 10,420,562 B2
(45) Date of Patent: Sep. 24, 2019

(54) BANDING DEVICE FOR TREATING HEMORRHOIDS AND RELOADING DEVICE

(71) Applicant: SpaceBander Corporation, Hillsborough, NJ (US)

(72) Inventor: Devjit S. Nayar, Hoboken, NJ (US)

(73) Assignees: Howard Loonan, Hillsborough, NJ (US); Steven Loonan, Wall, NJ (US)

( * ) Notice: Subject to any disclaimer, the term of this patent is extended or adjusted under 35 U.S.C. 154(b) by 343 days.

(21) Appl. No.: 15/049,498

(22) Filed: Feb. 22, 2016

(65) Prior Publication Data

US 2016/0242787 A1    Aug. 25, 2016

Related U.S. Application Data

(60) Provisional application No. 62/118,777, filed on Feb. 20, 2015.

(51) Int. Cl.
| | |
|---|---|
| *A61B 17/12* | (2006.01) |
| *A61B 17/128* | (2006.01) |
| *A61B 17/00* | (2006.01) |
| *A61B 17/30* | (2006.01) |
| *A61F 5/00* | (2006.01) |
| *A61B 90/00* | (2016.01) |

(52) U.S. Cl.
CPC ...... *A61B 17/12009* (2013.01); *A61B 17/128* (2013.01); *A61B 17/12013* (2013.01); *A61F 5/0093* (2013.01); *A61B 2017/00907* (2013.01); *A61B 2017/12004* (2013.01); *A61B 2017/12018* (2013.01); *A61B 2017/306* (2013.01); *A61B 2090/0808* (2016.02)

(58) Field of Classification Search
CPC .... A61B 2017/12018; A61B 17/12009; A61B 17/12; A61F 5/0093
See application file for complete search history.

(56) References Cited

U.S. PATENT DOCUMENTS 3,989,049 A * 11/1976 Yoon ................ A61B 17/12013
                                                        128/831
4,548,201 A * 10/1985 Yoon ...................... A61F 6/202
                                                        128/831
5,158,563 A    10/1992 Cosman
(Continued)

FOREIGN PATENT DOCUMENTS

| EP | 1683493 A1 | 7/2006 |
| EP | 2228022 A1 | 9/2010 |
| GB | 2443605 A  | 5/2008 |

OTHER PUBLICATIONS

International Search Report and Written Opinion corresponding to PCT/US2016/018948 dated Aug. 11, 2016, 8 pages.
(Continued)

*Primary Examiner* — Diane D Yabut
*Assistant Examiner* — Majid Jamialahmadi
(74) *Attorney, Agent, or Firm* — Gearhart Law, LLC.

(57) ABSTRACT

The application provides for an elastic band application ligation device. The following medical device medical device features an embowed inner tube, having a wall and a flat tip, a pusher which is complementarily shaped to said inner tube; and a receiving port, which is configured to removably attach to a device capable of generating suction. Preferably, this device capable of generating suction will be a disposable luer lock syringe.

17 Claims, 6 Drawing Sheets

(56) References Cited

U.S. PATENT DOCUMENTS

| | | | |
|---|---|---|---|
| 5,203,863 A * | 4/1993 | Bidoia | A61B 1/31 |
| | | | 604/902 |
| 5,464,412 A | 11/1995 | Budding | |
| 5,571,115 A | 11/1996 | Nicholas | |
| 5,741,273 A | 4/1998 | O'Regan | |
| 5,980,537 A | 11/1999 | Ouchi | |
| 6,342,052 B1 | 1/2002 | Allende | |
| 6,436,108 B1 | 8/2002 | Mears | |
| 6,896,682 B1 * | 5/2005 | McClellan | A61B 17/12013 |
| | | | 606/140 |
| 7,118,528 B1 | 10/2006 | Piskun | |
| 7,488,333 B2 | 2/2009 | Ghareeb | |
| 8,262,677 B2 | 9/2012 | Goto | |
| 8,591,525 B2 | 11/2013 | Ikeda | |
| 8,647,352 B2 | 2/2014 | Noda et al. | |
| 2002/0072757 A1 | 6/2002 | Ahmed et al. | |
| 2006/0259041 A1 * | 11/2006 | Hoffman | A61B 17/12013 |
| | | | 606/139 |
| 2009/0105728 A1 | 4/2009 | Noda et al. | |
| 2010/0063517 A1 * | 3/2010 | Cleator | A61B 17/12013 |
| | | | 606/140 |
| 2012/0010633 A1 | 1/2012 | Noda et al. | |
| 2012/0059394 A1 * | 3/2012 | Brenner | A61B 1/00087 |
| | | | 606/142 |
| 2013/0226198 A1 | 8/2013 | Kamler | |
| 2014/0121679 A1 | 1/2014 | Cleator | |

OTHER PUBLICATIONS

Supplementary Partial European Search Report, PCT/US2016/018948, dated Dec. 6, 2018, 16 pages.

* cited by examiner

BANDING DEVICE FOR TREATING HEMORRHOIDS AND RELOADING DEVICE

CLAIM OF PRIORITY

This application claims the priority of U.S. Ser. No. 62/118,777 filed on Feb. 20, 2015, the contents of which are fully incorporated herein by reference.

FIELD OF THE EMBODIMENTS

The invention and its embodiments relate to medical devices, namely an elastic band ligator. In particular, the present invention and its embodiments relate to an improved elastic band ligator for use in the treatment of hemorrhoids.

BACKGROUND OF THE EMBODIMENTS

Hemorrhoids are one of the most common issues in America today. Studies indicate that by the age of 50, 50% of Americans have been diagnosed with hemorrhoids. Hemorrhoids are clusters of swollen blood vessels that begin to swell into the alimentary canal of humans. At first hemorrhoids can easily go undetected, but if left alone can turn into the source of serious pain. Worse, if left unattended for a long enough period of time, hemorrhoids will begin to prolapse.

That is, untreated hemorrhoids will descend through the alimentary canal and extend through one's anus. Additionally, there exist "external" hemorrhoids which form not inside the alimentary canal, but around one's anus.

There are a number of different methods to treat and/or remove hemorrhoids, however, one such method, ligation, has gained popularity. Over the years, ligation is the act of closing off the blood vessels in the swollen hemorrhoid tissue. Over time, due to the lack of blood flow, the ligated hemorrhoid will eventually wither and fall off, painlessly. Ligation has been performed as early as 460 BC, however since then a number of apparatuses and methods have been developed to perform this task. That said, the prior art leaves a number of areas to be improved upon. For example, the devices taught by the prior art are notoriously difficult to operate with gloves on which is a prerequisite to ligating hemorrhoids. Further, the devices of the prior art are incapable of ligating hemorrhoids placed in the more remote areas of the alimentary canal.

Thus, there is a need for an elastic band ligation device that is easy to operate while wearing medical gloves, that also provides the ability to ligate the hard-to-reach places in a patient's alimentary canal. The present invention and its embodiments meet and exceed these objectives.

Review of related technology:

U.S. Pat. No. 5,741,273 pertains to an elastic band ligation device for that treatment of hemorrhoids. The device permits a doctor to band hemorrhoidal tissue without the help of an assistant and does not have to be attached to an aspirator. The device has the capability of suctioning tissue into a tubular member before banding. The device also has a plastic inner tubular member retains a stretched elastic band over a front end of an inner tubular member which extends for a sufficient length for insertion into the rectum of a patient. A plunger in the tubular member may be slid backwards to draw a suction in the tubular member to draw tissue in through the front end. A plastic outer pusher sleeve fits over the tubular member and is adapted to push the elastic band off the front end of the tubular member to capture the hemorrhoidal tissue drawn into the tubular member.

U.S. Patent Publication 2014/0121679 pertains to an elastic band ligation device for treating hemorrhoids and treatment method are provided. The device includes an inner tubular member for retaining an elastic band over the front end and the entire device is insertable into the rectum of a patient. The device is equipped with a plunger which generates suction for drawing hemorrhoidal tissue into the inner tubular member through the front end. A plastic outer tubular pusher sleeve has an arced configuration corresponding to the arcuate inner tubular member to provide a limited friction fit over the inner tubular member. The pusher sleeve is equipped with a thumb pusher to allow the outer tubular pusher sleeve to be pushed towards the front end of the inner tubular member and release the elastic band from the front end of the inner tubular member to engage hemorrhoidal tissue extending through the opening in the inner tubular member.

Various devices are known in the art. However, their structure and means of operation are substantially different from the present invention. Such devices fail to provide a device that can be easily operated through medical gloves and that provide a tool that can be used on a wider array of hemorrhoidal tissue. Further, the prior art teaches devices that are difficult to release suction with, provide for a poor fit within a patients rectum, and are so large that significant discomfort is caused in a patient being treated. At least one embodiment of this invention is presented in the drawings below and will be described in more detail herein.

SUMMARY OF THE EMBODIMENTS

The present invention provides for a medical device, comprising: an inner tube, having a wall and a flat tip, wherein said flat tip is comprised of an edge that is perpendicular to the walls of said inner tube; a pusher, complementarily shaped to said inner tube; and a receiving port, wherein said receiving port is configured to removably attach to a device capable of generating suction. Preferably, this device capable of generating suction is a luer lock syringe, and preferably said inner tube is embowed. In one embodiment, said pusher is permanently affixed to said inner tube and comes equipped with a plurality of protrusions. In some embodiments, the present invention is equipped with a reloader comprising: a conical frustum, an indentation, an a cylinder with at least one recessed flange.

In a preferred embodiment, the present invention is an elastic band ligation device, comprising: a curved inner tube, having a distal end, a proximate end, and a primary recessed flange located at said distal end; a pusher, wherein: said pusher is complementarily shaped to said curved inner tube, said pusher has a limited friction fit with the curved inner tube, said pusher is equipped with at least one protruding portion, and said pusher is equipped with a secondary recessed flange; and a receiving member, having an outer chamber, a receiving port located within said outer chamber, and a rear flange attached to said outer chamber, wherein said receiving port is configured to removably attach to a device capable of generating suction. In a preferred embodiment said pusher is capable of being extended at least 1 millimeter beyond the distal end of the inner rigid member.

In yet another embodiment, the present invention consists of a kit, comprising: a medical device, comprising: an inner tube, having a wall and a flat tip, wherein said flat tip is comprised of an edge that is perpendicular to the walls of said inner tube; a pusher, complementarily shaped to said inner tube; and a receiving port, wherein said receiving port is configured to removably couple to a device capable of generating suction; at least one elastic band; and a reloader, comprising: a bottom lip, a conical frustum section, a recessed flange, and a fitted opening, wherein said fitted opening is configured to receive the distal end of the curved inner tube.

Additionally, the present invention may be comprised of an inner tube, having a wall and a flat tip, wherein said flat tip is comprised of an edge that is perpendicular to the walls of said inner tube; a pusher, complementarily shaped to said inner tube; and a receiving port, wherein said receiving port is configured to removably attach to a syringe, preferably a luer lock syringe. In a preferred embodiment, this inner tube is embowed to allow for greater access to a patient's alimentary canal.

In yet another preferred embodiment, the inner tube and receiving port of the present invention are a single, unitary piece. This is intended to allow for the simplification of the manufacture of the present invention. In many embodiments, said pusher is engaged via a limited friction fit with the inner tube. This pusher may be equipped with a plurality of protrusions as well. In yet another preferred embodiment, the pusher is sized to extend at least one millimeter beyond the tip of the inner tube when extended.

The present invention also contemplates an elastic band reloader that works in conjunction with the medical device of the present invention. In a preferred embodiment, this reloader is comprised of a recessed flange, intended to be preloaded with an elastic band, a conical frustum section to allow for easy loading of the elastic band onto the medical device, and an indentation sized to receive the tip of the medical device of the present invention.

In general, the present invention succeeds in conferring the following, and other not mentioned, benefits and objectives.

The present invention has the benefit of the primary elastic band being preloaded on the device. This has the benefit of removing the difficult step found in the prior art, where an elastic band had to be manually loaded onto the ligator; something that is difficult while wearing medical gloves. Further, the embowed nature of the inner tube of the present invention allows for both easier insertion by the operator, and provides for increased comfort for the patient. Moreover, the inner tube of the present invention is significantly smaller than similar components found in the prior art, and said inner tube is equipped with a rounded flat tip, both of which provide for further increased comfort in a patient. Additionally, in a preferred embodiment, the present invention is entirely preassembled, providing for a sturdier product than that was is taught by the prior art.

It is an object of the present invention to provide a means for treating hemorrhoids.

It is an object of the present invention to provide a medical device.

It is an object of the present invention to provide an improved medical device for ligating hemorrhoids.

It is an object of the present invention to provide a medical device that is inexpensive and easy to use.

DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Figure 1:
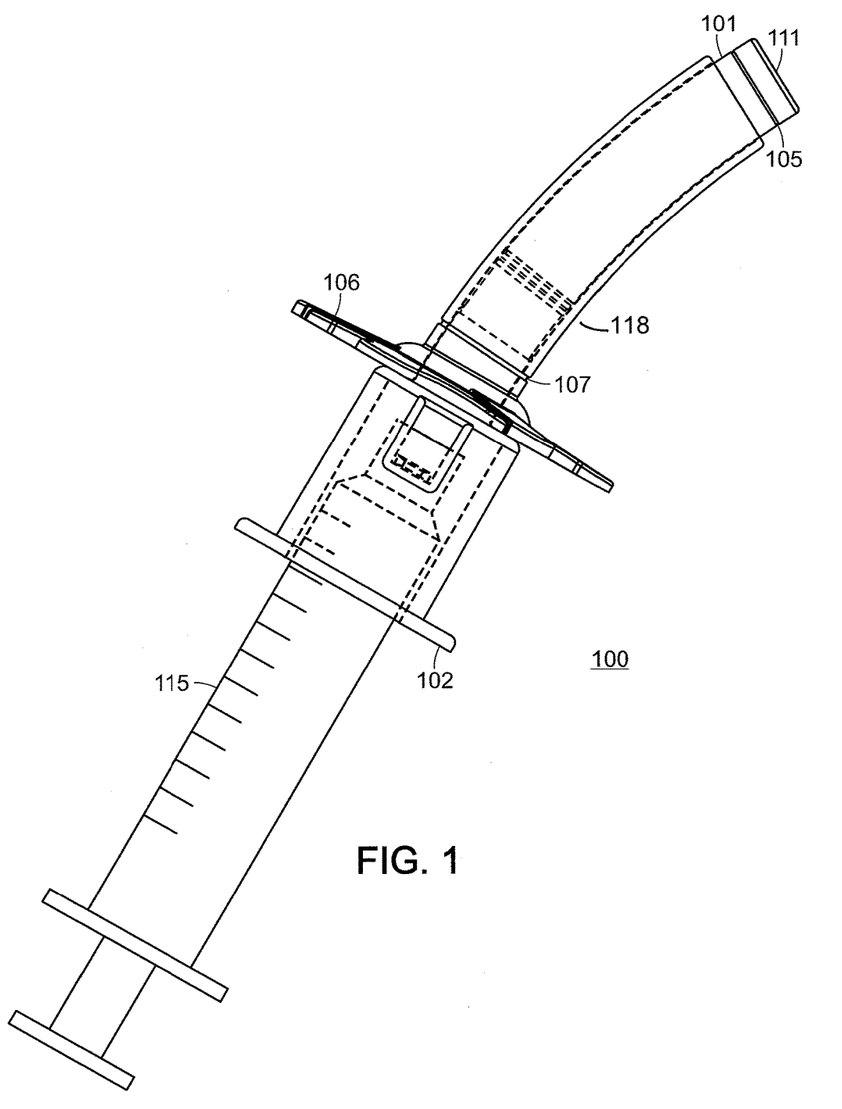
FIG. 1 is a front view of an embodiment of the present invention, wherein the present invention is removably attached to a standard luer lock syringe.

Referring to FIG. 1, a front view of an embodiment of the present invention is provided, wherein the present invention is removably attached to a standard luer lock syringe. Here, medical device 100 is shown. It is comprised of inner tube 101, which may be permanently affixed to pusher 106. Inner tube 101 is equipped with primary recessed flange 105. Primary recessed flange 105 is intended to, when loaded, house at least one elastic band (not pictured). In a preferred embodiment, to account for a failed deployment of an elastic band from the primary recessed flange 105, the present invention is equipped with secondary recessed flange 107.

Secondary recessed flange may be equipped with an elastic band such that it can be easily slid down pusher 106 onto primary recessed flange 105. This mechanism provides the additional benefit that it may be done easily while wearing medical gloves; something that is essential when hemorrhoid ligation is performed. In a preferred embodiment, medical device 100 is equipped with rear flange 102. This makes handling the present invention easier. Another feature of this particular embodiment is flat tip 111. Flat tip 111 allows for the consistent deployment of any elastic bands from primary recessed flange 105. The inclusion of flat tip 111 is particularly important when inner tube 101 is embowed. This is because the embowment of inner tube 101 allows for medical device 100 to reach previously unreachable areas of a patient's alimentary canal. In a preferred embodiment, medical device 100 operates by interfacing with a device that is capable of generating suction 115. Preferably, device capable of generating suction 115 is a luer lock syringe. Note that pusher 106 will engage with clicking stop point 118 such that it was informed the operator of the present invention that pusher 106 is in a position that provides for immediate deployment of at least one elastic band 117 (see FIG. 4 or 6). This is achieved by allowing pusher 106 to engage in a limited friction fit with inner tube 101. This feature has the benefit of preventing misfires, as well as allowing the operator to be certain of medical device's 100 position before deploying at least one elastic band 117. In an alternative embodiment, pusher 106 is equipped with bumps to allow for a tactile feel, increasing the dexterity in which medical device 100 may be operated with.

In one embodiment, once medical device 100 has interfaced with device capable of generating suction 115, it is equipped with an elastic band. Note that at least one elastic band may be comprised of latex, or a non-latex material. Medical device 100 is subsequently inserted into a patient's anus into the patient's alimentary canal. It should be noted that medical device 100 is suitable for treating external hemorrhoids, however, this description of use is for treatment of internal hemorrhoids. Once inserted into the patients alimentary canal, flat tip 111 is placed in close proximity to said hemorrhoid and device capable of generating suction 115 will generate suction, resulting in said hemorrhoid being drawn into inner tube 101. Once the hemorrhoid has been drawn into inner tube 101, pusher 106 is engaged and pushed beyond flat tip 111. This motion results in the loaded elastic band being wrapped around the base of said hemorrhoid. This placement of the elastic band will result in the hemorrhoid eventually falling off.

Figure 2:
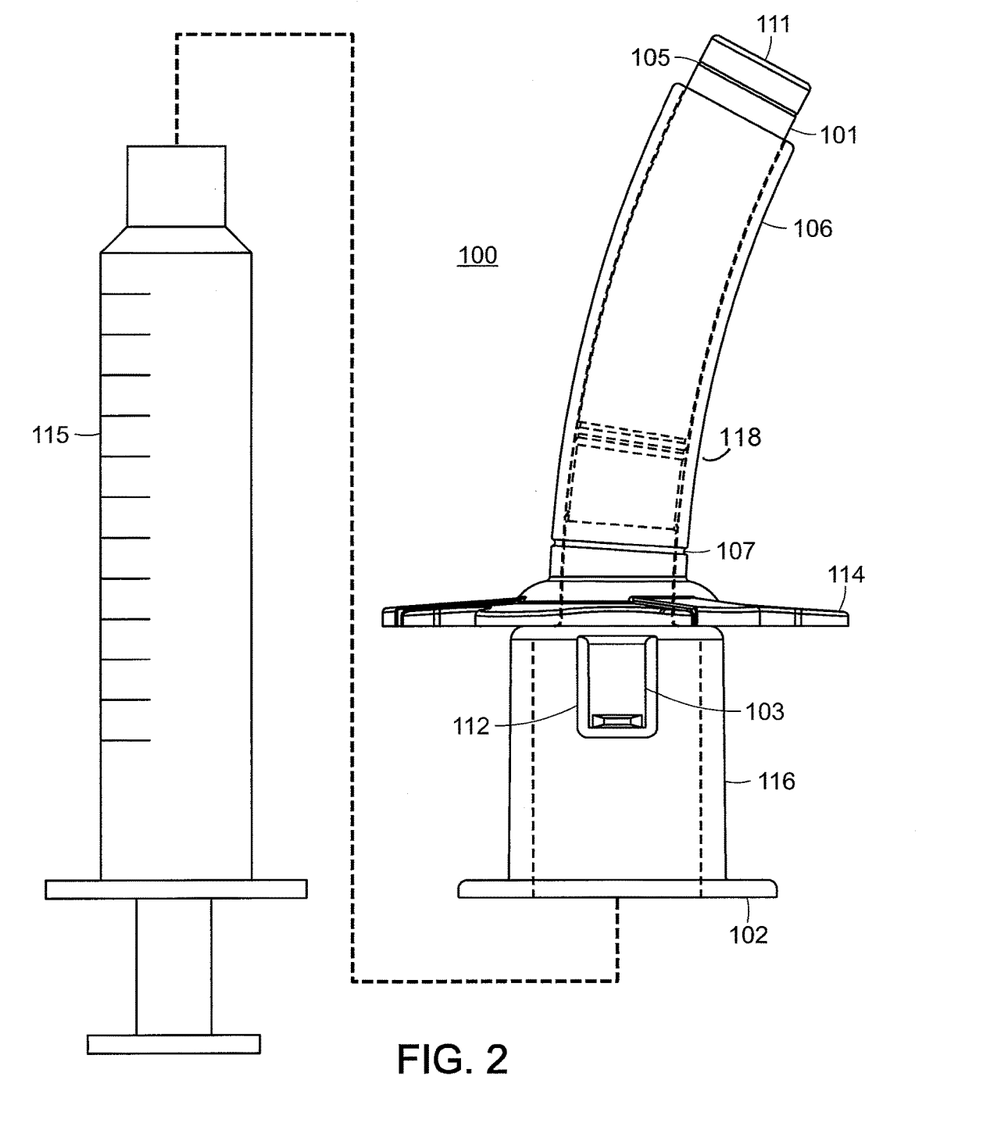
FIG. 2 is a front view of an embodiment of the invention, highlighting the removable nature of the present invention.

Referring to FIG. 2, a front view of an embodiment of the invention is shown, highlighting the removable nature of the present invention. Specifically, viewing port 112 and receiving port 103 are highlighted. Receiving port 103 is the aspect of the invention that interfaces with device capable of generating suction 115. When interfaced, these two components create a seal sufficient to support a vacuum capable of drawing a hemorrhoid within inner tube 101. Viewing port 112 is a feature of the present invention so that a user attempting to interface receiving port 103 with device that is capable of generating suction 115 may have a visual aid. Outer chamber 116 exists to help preserve the seal between receiving port 103 and device capable of generating suction 115. However, without the inclusion of viewing port 112, outer chamber 116 would inhibit the ease of interfacing between receiving port 103 and device capable of generating suction 115. This increases the efficiency of use of the present invention.

Also present in this figure are flat tip 111, primary recessed flange 105, inner tube 101, pusher 106, protrusions 114.

To use an alternative embodiment of the present invention, first device capable of generating suction 115, here a luer lock syringe, is screwed into receiving port 103. This provides for a seal between receiving port 103 and the luer lock syringe, allowing a vacuum to be generated near flat tip 111. Next, elastic band reloader 108 is accessed. If an elastic band is not present in cylinder with at least one recessed flange 109, an elastic band should be placed there. Then, elastic band reloader is used to load an elastic band onto primary recessed flange 105. Then, the luer lock syringe is engaged to draw the hemorrhoid inside of inner tube 101. From there, pusher 106 is used to slide the elastic band over the hemorrhoid.

Figure 3:
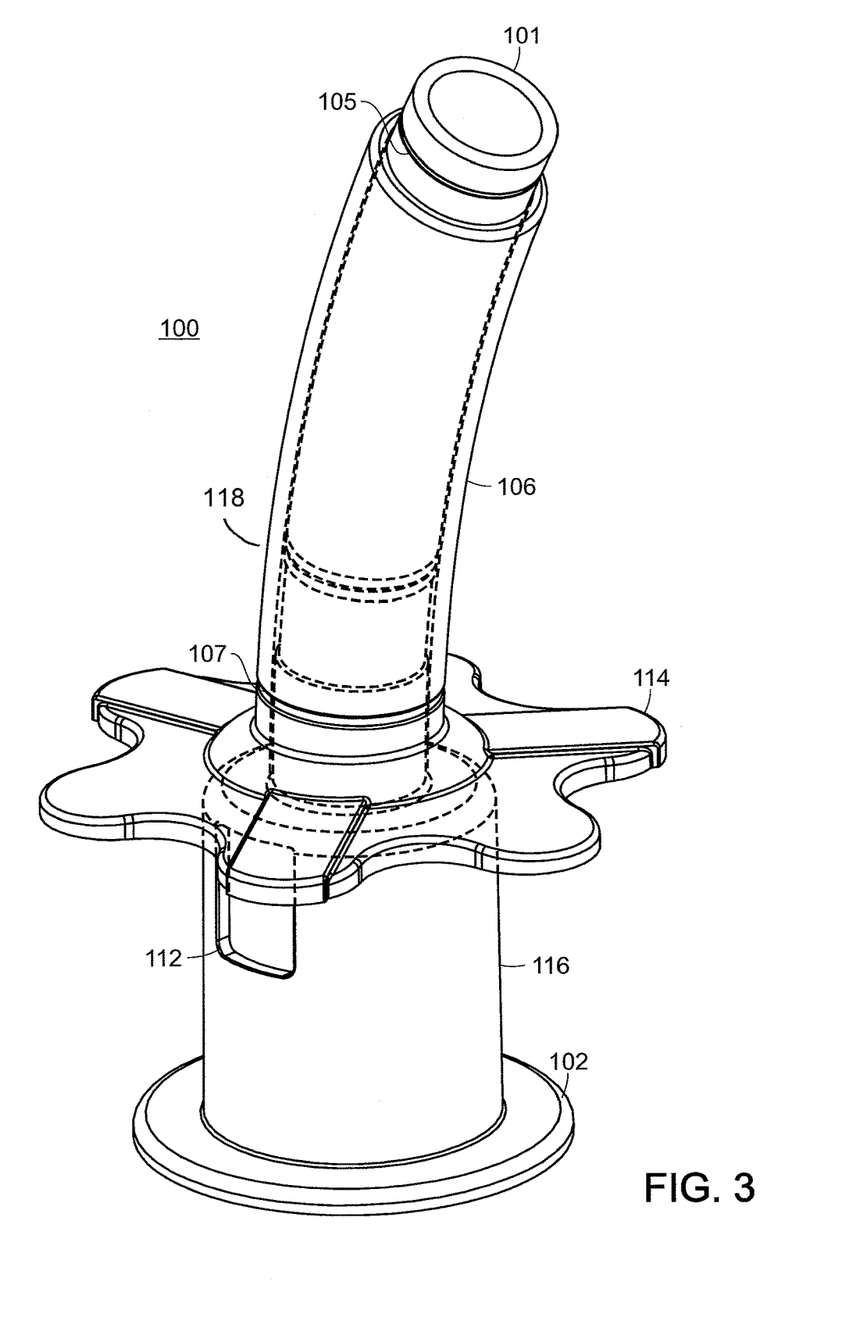
FIG. 3 is a perspective view of an embodiment of the invention.

FIG. 3 shows a perspective view of an embodiment of the invention. FIG. 3 highlights the relationship between inner tube 101 and pusher 106. Specifically, FIG. 3 shows that in a preferred embodiment, pusher 106 is shaped such that it creates a limited friction fit with inner tube 101. Protrusions 114 are also shown in FIG. 3. Protrusions 114 serve the purpose of providing a plurality of surfaces for a user to engage pusher 106 with. This is particularly beneficial in embodiments where inner tube 101 is embowed due to the fact that when in use, medical device 100 will likely be rotated after being inserted into a patient's alimentary canal. The embowment of inner tube 101 is also beneficial because it allows for a better fit around the patient's hemorrhoid, increasing the likelihood of success of the elastic band ligation. Having a plurality of protrusions will enable a user of medical device 100 to track the movement of the embowed inner tube 101, as well as provide ample surfaces to engage pusher 106 with. It should be noted that in a preferred embodiment, the position of protrusions 114 should not obstruct viewing port 112, and should not scrape against outer chamber 116.

Figure 4:
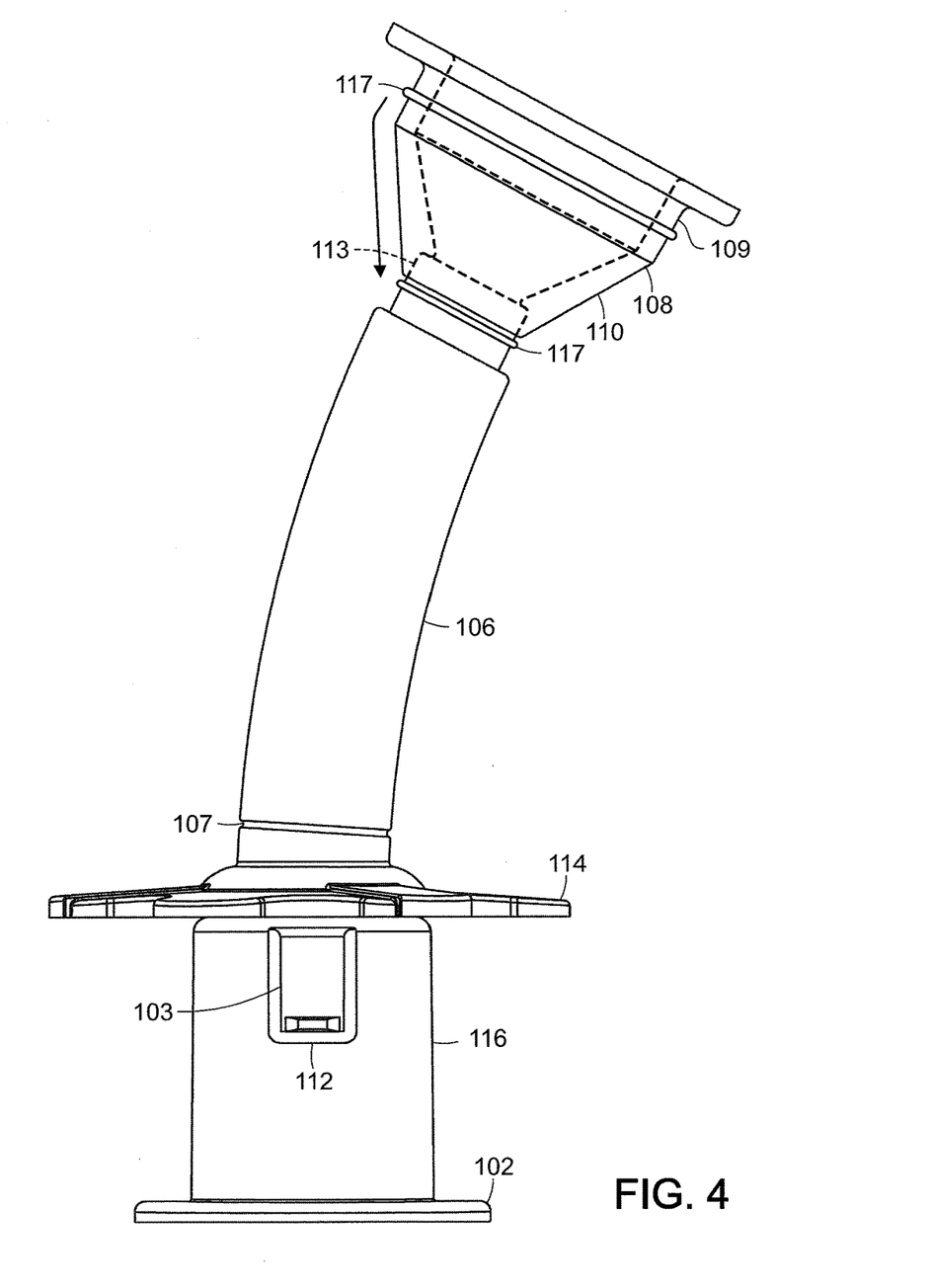
FIG. 4 is a perspective view of an embodiment of the present invention, wherein the medical device of the present invention is interfacing with the reloader of the present invention.

Referring to FIG. 4, a perspective view of an embodiment of the present invention is provided, wherein the medical device of the present invention is interfacing with the reloader of the present invention. Medical device 100 interfaces with elastic band reloader 108 by having flat tip 111 inserted into indentation 113. It is not imperative that any kind of seal be maintained at this junction, merely that the fit is tight enough that at least one elastic band 117 may be easily loaded onto primary recessed flange 105 (not shown) by sliding down conical frustum 110. The elasticity of at least one elastic band 117 will hold at least one elastic band 117 to inner tube 101 (not shown) when loaded. In a preferred embodiment, at least one elastic band 117 is preloaded onto cylinder with at least one recessed flange 109. In another preferred embodiment, elastic band loader 108 is shaped such that it may be used to load elastic bands onto secondary recessed flange 107. There, pusher 106 would interface with indentation 113, again forming a seal such that at least one elastic band 117 may slide down conical frustum 110, as well as pusher 106 down to secondary recessed flange 107 (not shown). Also of note here is the relationship between receiving port 103 and viewing port 112. In one embodiment, viewing port 112 is sized such that the entirety of receiving port 103 is visible through viewing port 112.

In a preferred embodiment, secondary recessed flange 107 and elastic band reloader 108 are preloaded with elastic bands. In an alternative embodiment, secondary recessed flange 107 and primary recessed flange 105 are both preloaded with elastic bands. Preferably, these bands will be located on secondary recessed flange 107 and cylinder with at least one recessed flange 109. There, flat tip 111 is inserted into indentation 113. This creates a substantially flush surface between conical frustum 110 and inner tube 101, providing for an easy means to load the elastic band onto primary recessed flange 105.

Figure 5:
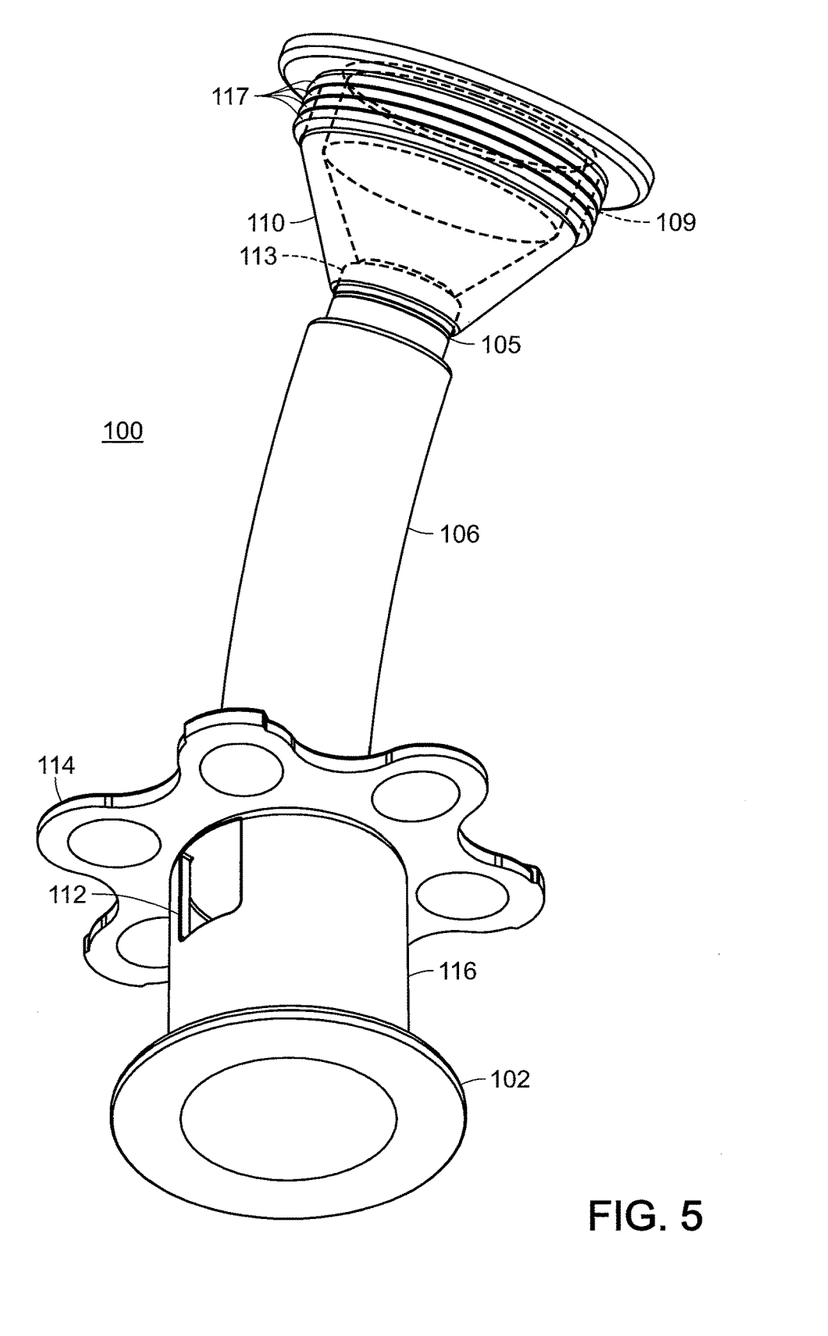
FIG. 5 is a top view of an embodiment of the present invention, illustrating the reloading mechanism.

Regarding FIG. 5, a top view of an embodiment of the present invention is shown, illustrating the reloading mechanism. Here, the fact that more than one of the at least one elastic band 117 may be loaded onto cylinder with at least one recessed flange 109, and that primary recessed flange 105 is also capable of receiving more than one of the at least one elastic band 117. In an alternative embodiment, secondary recessed flange 107 is also capable of receiving more than one of the at least one elastic band 117.

Figure 6:
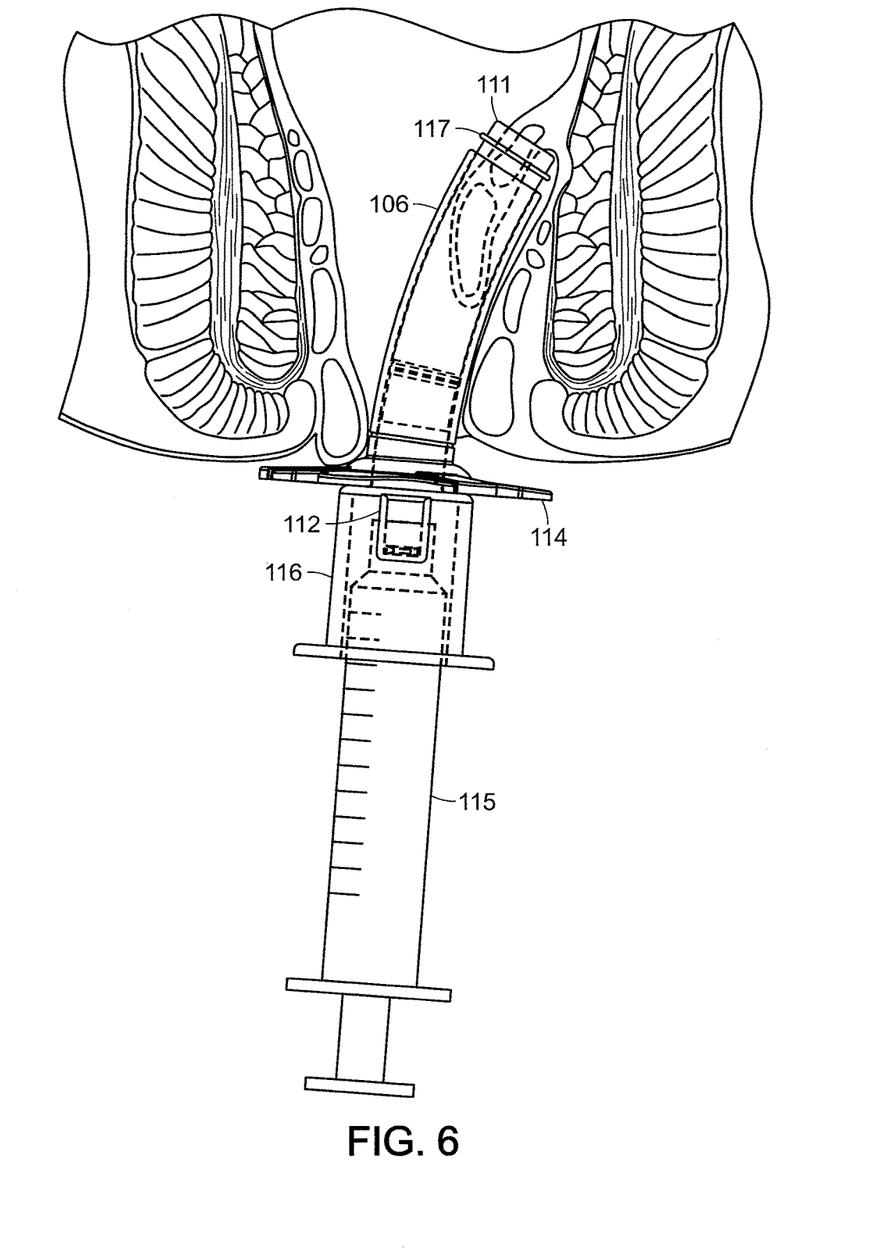
FIG. 6 is an illustration of the present invention in use is provided.

Referring to FIG. 6, an illustration of the present invention in use is provided. The process illustrated here involved places flat tip 111 in close proximity to a hemorrhoid to be treated. Device capable of generating suction 115 then generates suction, drawing the hemorrhoid within inner tube 101. Pusher 106 is subsequently engaged resulting in at least one elastic band 117 being wrapped around said hemorrhoid. The suction is then turned off and medical device 100 is removed from the patient. This view illustrates the benefit of protrusions 114, as it gives a number of different surfaces to begin the deployment of at least one elastic band 117.

When introducing elements of the present disclosure or the embodiment(s) thereof, the articles "a," "an," and "the"

are intended to mean that there are one or more of the elements. Similarly, the adjective "another," when used to introduce an element, is intended to mean one or more elements. The terms "including" and "having" are intended to be inclusive such that there may be additional elements other than the listed elements.

While the disclosure refers to exemplary embodiments, it will be understood by those skilled in the art that various changes may be made and equivalents may be substituted for elements thereof without departing from the scope of the disclosure. In addition, many modifications will be appreciated by those skilled in the art to adapt a particular instrument, situation or material to the teachings of the disclosure without departing from the spirit thereof. Therefore, it is intended that the disclosure not be limited to the particular embodiments disclosed.

What is claimed is:

1. A medical device, comprising:
    an embowed inner tube, having a wall, a first recessed flange, and a flat tip,
        wherein said flat tip is comprised of an edge that is perpendicular to the wall of said inner tube;
    a pusher having a second recessed flange disposed thereon, the pusher being complementarily shaped to and slidably engaged with said embowed inner tube,
        wherein a stop point of the pusher is configured to engage in a stop point of said embowed inner tube;
    a receiving member, having a circular outer chamber, at least one viewing port, and a receiving port,
        wherein said at least one viewing port is disposed in a sidewall of said circular outer chamber; and
    a syringe configured to be removably coupled to the receiving port,
        wherein the syringe is configured to generate suction.

2. The medical device of claim 1, wherein said syringe is a luer lock syringe.

3. The medical device of claim 1, wherein said embowed inner tube and said receiving port are comprised of a solitary construction.

4. The medical device of claim 1, wherein said pusher is permanently affixed to said embowed inner tube.

5. The medical device of claim 1, wherein said pusher is equipped with a plurality of protrusions.

6. The medical device of claim 1, further comprising an elastic band reloader.

7. The medical device of claim 6, wherein said elastic band reloader further comprises:
    an indentation, shaped to receive said flat tip.

8. The medical device of claim 6, said elastic band reloader further comprising:
    a conical frustum.

9. The medical device of claim 6, further comprising at least one elastic band;
    wherein said elastic band reloader is equipped with a third recessed flange; and
    wherein said at least one elastic band is preloaded on the third recessed flange of the elastic band reloader.

10. The medical device of claim 1, wherein said pusher is capable of extending at least 1 millimeter beyond said flat tip of the inner tube.

11. An elastic band ligation device, comprising:
    a curved inner tube, having a distal end, a proximate end, and a primary recessed flange located at said distal end;
    a pusher,
        wherein:
            said pusher is complementarily shaped to said curved inner tube,
            a stop point of said pusher is configured to engage a stop point of said curved inner tube,
            said pusher is equipped with a plurality of protruding portions, and
            said pusher is equipped with a secondary recessed flange; and
    a receiving member, having a circular outer chamber, at least one viewing port, a receiving port located within said circular outer chamber, and a rear flange extending perpendicularly from said circular outer chamber,
        wherein said at least one viewing port is disposed in a sidewall of said circular outer chamber, and
        wherein said at least one viewing port is aligned with said receiving port; and
    a syringe configured to removably couple to the receiving port, the syringe being configured to generate suction.

12. The elastic band ligation device of claim 11, further comprising:
    a loader, having a conical frustum section, a third recessed flange, and a fitted opening,
        wherein said fitted opening is configured to receive the distal end of the curved inner tube.

13. The elastic band ligation device of claim 12, further comprising an elastic band preloaded in the third recessed flange.

14. The elastic band ligation device of claim 11, wherein said pusher is capable of being extended at least 1 millimeter beyond the distal end of the curved inner tube.

15. The elastic band ligation device of claim 14, wherein said curved inner tube further comprises a tip, wherein said tip is perpendicular to a wall of said curved inner tube.

16. A kit, comprising:
    a medical device, comprising:
        a curved inner tube, having a wall and a flat tip,
            wherein said flat tip is comprised of an edge that is perpendicular to the wall of said inner tube;
        a pusher having a first recessed flange disposed thereon, the pusher complementarily shaped to said inner tube,
            said pusher configured to engage a stop point of said curved inner tube; and
        a receiving member having a circular outer chamber, at least one viewing port, a receiving port located within said circular outer chamber, and a rear flange extending perpendicularly from said circular outer chamber,
            wherein said receiving port is configured to removably couple to a device capable of generating suction, and
            wherein said at least one viewing port is disposed in a sidewall of said circular outer chamber; and
    at least one elastic band.

17. The kit of claim 16 further comprising:
    a reloader, comprising:
        a conical frustum section, a second recessed flange, and a fitted opening,
            wherein said fitted opening is configured to receive a distal end of the inner tube.

* * * * *